United States Patent
Felt et al.

(10) Patent No.: US 11,491,023 B2
(45) Date of Patent: *Nov. 8, 2022

(54) METHODS AND APPARATUS FOR MINIMALLY INVASIVE MODULAR INTERBODY FUSION DEVICES

(71) Applicant: Next Orthosurgical, Inc., Vista, CA (US)

(72) Inventors: Jeffrey C. Felt, Greenwood, MN (US); Britt Norton, Eden Prairie, MN (US); Mark A. Rydell, Golden Valley, MN (US); Stephen H. Crosbie, Prior Lake, MN (US)

(73) Assignee: Next Orthosurgical, Inc., Vista, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/266,788

(22) Filed: Feb. 4, 2019

(65) Prior Publication Data

US 2019/0269524 A1    Sep. 5, 2019

Related U.S. Application Data

(63) Continuation of application No. 15/682,033, filed on Aug. 21, 2017, now Pat. No. 10,195,048, which is a
(Continued)

(51) Int. Cl.
*A61F 2/44* (2006.01)
*A61F 2/46* (2006.01)
(Continued)

(52) U.S. Cl.
CPC .......... *A61F 2/4465* (2013.01); *A61F 2/4611* (2013.01); *A61F 2/0095* (2013.01);
(Continued)

(58) Field of Classification Search
CPC ........ A61F 2002/448; A61F 2002/4485; A61F 2/4455; A61F 2/446; A61F 2/4465;
(Continued)

(56) References Cited

U.S. PATENT DOCUMENTS 3,030,951 A    4/1962 Mandarino
3,728,742 A    4/1973 Averill et al.
(Continued)

FOREIGN PATENT DOCUMENTS

CN    101193608    6/2008
EP    0 353 936    2/1990
(Continued)

OTHER PUBLICATIONS

Application and File history for U.S. Appl. No. 11/974,185, filed Oct. 11, 2007, inventors Felt et al.
(Continued)

*Primary Examiner* — Jan Christopher L Merene (57) ABSTRACT

The invention is a modular interbody fusion device for fusing adjacent spinal vertebrae that is adapted to be implanted in a prepared interbody space including a first modular segment having a width including a first rail extending at least partially along one side of the width and beyond a periphery of a body portion of the first modular segment, a second modular segment having a width and slidably connected to the first rail on one side of the width and having a second rail extending at least partially along another side of the width and beyond a periphery of a body portion of the second modular segment, a third modular segment having a width and slidably connected to the second rail on one side of the width and wherein the device has an expanded position in which the second and third modular segments are extended along the first and second rails and positioned in a generally end to end configuration
(Continued)

spaced apart by the rails prior to implantation and an implanted position in which the modular segments are positioned in a generally side by side configuration that defines a unitary body that mimics the planar shape of the vertebra such that the device contacts and supports the adjacent vertebra.

9 Claims, 2 Drawing Sheets

Related U.S. Application Data continuation of application No. 11/974,185, filed on Oct. 11, 2007, now Pat. No. 9,737,414.

(60) Provisional application No. 60/860,329, filed on Nov. 21, 2006.

(51) Int. Cl.
    *A61F 2/00*         (2006.01)
    *A61F 2/28*         (2006.01)
    *A61F 2/30*         (2006.01)

(52) U.S. Cl.
CPC .............. *A61F 2002/2835* (2013.01); *A61F 2002/3008* (2013.01); *A61F 2002/30062* (2013.01); *A61F 2002/30383* (2013.01); *A61F 2002/30522* (2013.01); *A61F 2002/30593* (2013.01); *A61F 2002/30604* (2013.01); *A61F 2002/30677* (2013.01); *A61F 2002/30841* (2013.01); *A61F 2002/4629* (2013.01); *A61F 2210/0004* (2013.01); *A61F 2220/0025* (2013.01); *A61F 2250/0098* (2013.01); *A61F 2310/00023* (2013.01)

(58) Field of Classification Search
CPC ............... A61F 2/447; A61F 2/4611; A61F 2002/30604; A61F 2002/30387
See application file for complete search history.

(56) References Cited

U.S. PATENT DOCUMENTS

| | | |
|---|---|---|
| 3,815,599 A | 6/1974 | Deyerle |
| 3,848,601 A | 11/1974 | Ma et al. |
| 3,867,728 A | 2/1975 | Stubstad et al. |
| 3,867,729 A | 2/1975 | Stubstad et al. |
| 4,081,866 A | 4/1978 | Upshaw et al. |
| 4,203,444 A | 5/1980 | Bonnell et al. |
| 4,349,921 A | 9/1982 | Kuntz |
| 4,456,745 A | 6/1984 | Rajan |
| 4,463,141 A | 7/1984 | Robinson |
| 4,476,293 A | 10/1984 | Robinson |
| 4,477,604 A | 10/1984 | Oechsle, III |
| 4,502,161 A | 3/1985 | Wall |
| 4,647,643 A | 3/1987 | Zdrahala et al. |
| 4,651,736 A | 3/1987 | Sanders |
| 4,711,639 A | 12/1987 | Grundei |
| 4,722,948 A | 2/1988 | Sanderson |
| 4,743,256 A | 5/1988 | Brantigan |
| 4,743,632 A | 5/1988 | Marinovic |
| 4,772,287 A | 9/1988 | Ray et al. |
| 4,808,691 A | 2/1989 | Konig et al. |
| 4,834,757 A | 5/1989 | Brantigan |
| 4,863,476 A | 9/1989 | Shepperd |
| 4,873,308 A | 10/1989 | Coury et al. |
| 4,880,610 A | 11/1989 | Constantz |
| 4,904,260 A | 2/1990 | Ray et al. |
| 4,911,718 A | 3/1990 | Lee et al. |
| 4,969,888 A | 11/1990 | Scholten et al. |
| 5,007,940 A | 4/1991 | Berg |
| 5,047,055 A | 9/1991 | Bao et al. |
| 5,067,964 A | 11/1991 | Richmond et al. |
| 5,082,803 A | 1/1992 | Sumita |
| 5,108,404 A | 4/1992 | Scholten et al. |
| 5,109,077 A | 4/1992 | Wick |
| 5,143,942 A | 9/1992 | Brown |
| 5,166,115 A | 11/1992 | Brown |
| 5,192,326 A | 3/1993 | Bao et al. |
| 5,192,327 A | 3/1993 | Brantigan |
| 5,254,662 A | 10/1993 | Szycher et al. |
| 5,263,987 A | 11/1993 | Shah |
| 5,278,201 A | 1/1994 | Dunn et al. |
| 5,344,458 A | 9/1994 | Bonutti |
| 5,344,459 A | 9/1994 | Swartz |
| 5,397,364 A | 3/1995 | Kozak et al. |
| 5,458,643 A | 10/1995 | Oka et al. |
| 5,509,934 A | 4/1996 | Cohen |
| 5,514,180 A | 5/1996 | Heggeness |
| 5,522,899 A | 6/1996 | Michelson |
| 5,525,418 A | 6/1996 | Hashimoto et al. |
| 5,545,229 A | 8/1996 | Parsons et al. |
| 5,549,683 A | 8/1996 | Bonutti |
| 5,554,191 A | 9/1996 | Lahille et al. |
| 5,556,429 A | 9/1996 | Felt |
| 5,562,736 A | 10/1996 | Ray et al. |
| 5,609,635 A | 3/1997 | Michelson |
| 5,624,463 A | 4/1997 | Stone et al. |
| 5,674,294 A | 10/1997 | Bainville et al. |
| 5,702,453 A | 12/1997 | Rabbe et al. |
| 5,702,454 A | 12/1997 | Baumgartner |
| 5,725,531 A | 3/1998 | Shapiro |
| 5,755,797 A | 5/1998 | Baumgartner |
| 5,772,661 A | 6/1998 | Michelson |
| 5,776,199 A | 7/1998 | Michelson |
| 5,795,353 A | 8/1998 | Felt |
| 5,800,547 A | 9/1998 | Schafer et al. |
| 5,824,093 A | 10/1998 | Ray et al. |
| 5,860,973 A | 1/1999 | Michelson |
| 5,861,041 A | 1/1999 | Tienboon et al. |
| 5,888,220 A | 3/1999 | Felt et al. |
| 5,888,227 A | 3/1999 | Cottle |
| 5,888,228 A | 3/1999 | Knothe et al. |
| 5,893,889 A | 4/1999 | Harringson |
| 5,919,236 A | 7/1999 | Pfaff et al. |
| 5,944,759 A | 8/1999 | Link |
| 5,980,522 A | 11/1999 | Koros et al. |
| 5,989,289 A | 11/1999 | Coates et al. |
| 5,989,291 A | 11/1999 | Ralph et al. |
| 6,033,438 A | 3/2000 | Bianchi et al. |
| 6,048,345 A | 4/2000 | Berke et al. |
| 6,079,868 A | 6/2000 | Rydell |
| 6,080,193 A | 6/2000 | Hochshuler et al. |
| 6,096,038 A | 8/2000 | Michelson |
| 6,096,080 A | 8/2000 | Nicholson et al. |
| 6,102,950 A | 8/2000 | Vaccaro |
| 6,110,210 A | 8/2000 | Norton et al. |
| 6,113,638 A | 9/2000 | Williams et al. |
| 6,117,174 A | 9/2000 | Nolan |
| 6,132,472 A | 10/2000 | Bonutti |
| 6,139,579 A | 10/2000 | Steffee et al. |
| 6,140,452 A | 10/2000 | Felt et al. |
| 6,143,033 A | 11/2000 | Paul et al. |
| 6,146,422 A | 11/2000 | Lawson |
| 6,159,211 A | 12/2000 | Boriani et al. |
| 6,174,311 B1 | 1/2001 | Branch et al. |
| 6,176,882 B1 | 1/2001 | Biedermann et al. |
| 6,183,517 B1 | 2/2001 | Suddaby |
| 6,190,414 B1 | 2/2001 | Young et al. |
| 6,206,923 B1 | 3/2001 | Boyd et al. |
| 6,206,927 B1 | 3/2001 | Fell et al. |
| 6,224,630 B1 | 5/2001 | Bao et al. |
| 6,224,631 B1 | 5/2001 | Kohrs |
| 6,245,108 B1 | 6/2001 | Biscup |
| 6,248,131 B1 | 6/2001 | Felt et al. |
| 6,251,140 B1 | 6/2001 | Marino et al. |
| 6,258,125 B1 | 7/2001 | Paul et al. |
| 6,264,695 B1 | 7/2001 | Stoy |
| 6,270,528 B1 | 8/2001 | McKay |
| 6,302,914 B1 | 10/2001 | Michelson |
| 6,342,075 B1 | 1/2002 | MacArthur |

(56) References Cited

U.S. PATENT DOCUMENTS

| | | | |
|---|---|---|---|
| 6,348,071 B1 | 2/2002 | Steffee et al. | |
| 6,371,988 B1 | 4/2002 | Pafford et al. | |
| 6,371,990 B1 | 4/2002 | Ferree | |
| 6,387,130 B1 | 5/2002 | Stone et al. | |
| 6,419,704 B1 | 7/2002 | Ferree | |
| 6,419,705 B1 | 7/2002 | Erickson | |
| 6,436,140 B1 | 8/2002 | Liu et al. | |
| 6,436,143 B1 | 8/2002 | Ross et al. | |
| 6,440,169 B1 | 8/2002 | Elberg et al. | |
| 6,443,988 B2 | 9/2002 | Felt et al. | |
| 6,468,311 B2 | 10/2002 | Boyd et al. | |
| 6,488,710 B2 | 12/2002 | Besselink | |
| 6,511,509 B1 | 1/2003 | Ford et al. | |
| 6,524,341 B2 | 2/2003 | Lang et al. | |
| 6,533,818 B1 | 3/2003 | Weber et al. | |
| 6,537,280 B2 | 3/2003 | Dinger et al. | |
| 6,558,421 B1 | 5/2003 | Fell et al. | |
| 6,558,424 B2 | 5/2003 | Thalgott | |
| 6,562,074 B2 | 5/2003 | Gerbec et al. | |
| 6,595,998 B2 | 7/2003 | Johnson et al. | |
| 6,610,092 B2 | 8/2003 | Ralph et al. | |
| 6,610,093 B1 | 8/2003 | Pisharodi | |
| 6,620,196 B1 | 9/2003 | Trieu | |
| 6,648,917 B2 | 11/2003 | Gerbec et al. | |
| 6,652,587 B2 | 11/2003 | Felt et al. | |
| 6,669,732 B2 | 12/2003 | Serhan et al. | |
| 6,726,720 B2 | 4/2004 | Ross et al. | |
| 6,726,721 B2 | 4/2004 | Stoy et al. | |
| 6,733,535 B2 | 5/2004 | Michelson | |
| 6,740,093 B2 | 5/2004 | Hochschuler et al. | |
| 6,764,514 B1 | 7/2004 | Li et al. | |
| 6,770,095 B2 | 8/2004 | Grinberg et al. | |
| 6,773,460 B2 | 8/2004 | Jackson | |
| 6,793,678 B2 | 9/2004 | Hawkins | |
| 6,821,298 B1 | 11/2004 | Jackson | |
| 6,835,206 B2 | 12/2004 | Jackson | |
| 6,852,129 B2 | 2/2005 | Gerbec et al. | |
| 6,855,165 B2 | 2/2005 | Fell et al. | |
| 6,855,167 B2 | 2/2005 | Shimp et al. | |
| 6,866,684 B2 | 3/2005 | Fell et al. | |
| 6,893,463 B2 | 5/2005 | Fell et al. | |
| 6,896,701 B2 | 5/2005 | Boyd et al. | |
| 6,911,044 B2 | 6/2005 | Fell et al. | |
| 6,923,831 B2 | 8/2005 | Fell et al. | |
| 6,966,928 B2 | 11/2005 | Fell et al. | |
| 7,001,431 B2 | 2/2006 | Bao et al. | |
| 7,008,452 B2 | 3/2006 | Hawkins | |
| 7,018,416 B2 | 3/2006 | Hanson et al. | |
| 7,037,339 B2 | 5/2006 | Houfburg | |
| 7,238,204 B2 | 7/2007 | Le Couedic et al. | |
| 7,267,690 B2 | 9/2007 | Felt | |
| 7,291,171 B2 | 11/2007 | Ferree | |
| 7,297,161 B2 | 11/2007 | Fell | |
| 7,320,709 B2 | 1/2008 | Felt et al. | |
| 7,341,602 B2 | 3/2008 | Fell et al. | |
| 7,491,235 B2 | 2/2009 | Fell | |
| 7,491,237 B2 | 2/2009 | Randall et al. | |
| 7,563,285 B2 | 7/2009 | Ralph et al. | |
| 7,591,853 B2 | 9/2009 | Felt et al. | |
| 7,618,458 B2 | 11/2009 | Biedermann et al. | |
| 7,621,960 B2 | 11/2009 | Boyd et al. | |
| 7,666,228 B2 | 2/2010 | Le Couedic et al. | |
| 7,914,582 B2 | 3/2011 | Felt et al. | |
| 8,038,718 B2 | 10/2011 | Palm et al. | |
| 8,100,977 B2 | 1/2012 | Felt | |
| 8,828,019 B1 | 9/2014 | Raymond et al. | |
| 9,510,953 B2 | 12/2016 | Felt et al. | |
| 9,737,414 B2 | 8/2017 | Felt et al. | |
| 2001/0004710 A1 | 6/2001 | Felt et al. | |
| 2001/0047207 A1 | 11/2001 | Michelson | |
| 2002/0026244 A1 | 2/2002 | Trieu | |
| 2002/0029084 A1 | 3/2002 | Paul et al. | |
| 2002/0055742 A1* | 5/2002 | Lieberman | A61F 2/44 606/301 |
| 2002/0099444 A1 | 7/2002 | Boyd et al. | |
| 2002/0127264 A1 | 9/2002 | Felt et al. | |
| 2002/0128713 A1 | 9/2002 | Ferree | |
| 2002/0183850 A1 | 12/2002 | Felt et al. | |
| 2003/0055506 A1 | 3/2003 | Stoy et al. | |
| 2003/0065396 A1 | 4/2003 | Michelson | |
| 2003/0109928 A1 | 6/2003 | Pasquet | |
| 2003/0125739 A1 | 7/2003 | Bagga et al. | |
| 2003/0130739 A1 | 7/2003 | Gerbec et al. | |
| 2003/0135279 A1 | 7/2003 | Michelson | |
| 2003/0220691 A1 | 11/2003 | Songer et al. | |
| 2003/0230198 A1 | 12/2003 | Zitttel | |
| 2003/0233147 A1* | 12/2003 | Nicholson | A61F 2/4611 623/17.16 |
| 2003/0236571 A1 | 12/2003 | Ralph et al. | |
| 2004/0002761 A1 | 1/2004 | Rogers et al. | |
| 2004/0006393 A1 | 1/2004 | Burkinshaw | |
| 2004/0010318 A1 | 1/2004 | Ferree | |
| 2004/0019354 A1 | 1/2004 | Johnson et al. | |
| 2004/0049280 A1* | 3/2004 | Cauthen | A61F 2/4425 623/17.14 |
| 2004/0054413 A1 | 3/2004 | Higham et al. | |
| 2004/0059421 A1 | 3/2004 | Glenn et al. | |
| 2004/0064144 A1 | 4/2004 | Johnson et al. | |
| 2004/0111155 A1 | 6/2004 | Ferree | |
| 2004/0127994 A1 | 7/2004 | Kast et al. | |
| 2004/0162618 A1 | 8/2004 | Mujwid et al. | |
| 2004/0172134 A1 | 9/2004 | Berry | |
| 2004/0186576 A1 | 9/2004 | Biscup et al. | |
| 2004/0220580 A1 | 11/2004 | Johnson et al. | |
| 2004/0220672 A1 | 11/2004 | Shadduck | |
| 2004/0225363 A1 | 11/2004 | Richelsoph | |
| 2004/0230198 A1 | 11/2004 | Manzi et al. | |
| 2004/0267366 A1 | 12/2004 | Kruger | |
| 2004/0267367 A1 | 12/2004 | O'Neil | |
| 2005/0010290 A1 | 1/2005 | Hawkins | |
| 2005/0010295 A1 | 1/2005 | Michelson | |
| 2005/0015150 A1 | 1/2005 | Lee | |
| 2005/0033424 A1 | 2/2005 | Fell | |
| 2005/0055097 A1 | 3/2005 | Grunberg et al. | |
| 2005/0080489 A1* | 4/2005 | Estes | A61F 2/4455 623/17.16 |
| 2005/0131543 A1 | 6/2005 | Benzel et al. | |
| 2005/0154463 A1 | 7/2005 | Trieu | |
| 2005/0154465 A1 | 7/2005 | Trieu | |
| 2005/0187633 A1 | 8/2005 | Ferree | |
| 2005/0203599 A1 | 9/2005 | Garabedian et al. | |
| 2005/0228500 A1 | 10/2005 | Kim et al. | |
| 2005/0234555 A1 | 10/2005 | Sutton et al. | |
| 2005/0240267 A1 | 10/2005 | Randall et al. | |
| 2005/0273178 A1 | 12/2005 | Boyan et al. | |
| 2006/0004454 A1 | 1/2006 | Ferree et al. | |
| 2006/0025861 A1 | 2/2006 | McKay | |
| 2006/0058807 A1 | 3/2006 | Landry et al. | |
| 2006/0058880 A1 | 3/2006 | Wysocki et al. | |
| 2006/0069438 A1 | 3/2006 | Zucherman et al. | |
| 2006/0106462 A1 | 5/2006 | Tsou | |
| 2006/0142858 A1 | 6/2006 | Colleran et al. | |
| 2006/0142862 A1 | 6/2006 | Diaz et al. | |
| 2006/0149383 A1 | 7/2006 | Arnin et al. | |
| 2006/0167550 A1 | 7/2006 | Snell et al. | |
| 2006/0173542 A1 | 8/2006 | Shikinami | |
| 2006/0178745 A1 | 8/2006 | Bartish et al. | |
| 2006/0189999 A1 | 8/2006 | Zwirkoski | |
| 2006/0190083 A1 | 8/2006 | Arnin et al. | |
| 2006/0195191 A1 | 8/2006 | Sweeney et al. | |
| 2006/0212118 A1 | 9/2006 | Abernathie | |
| 2006/0235535 A1 | 10/2006 | Ferree et al. | |
| 2006/0247778 A1 | 11/2006 | Ferree et al. | |
| 2006/0247781 A1 | 11/2006 | Francis | |
| 2006/0259144 A1 | 11/2006 | Trieu | |
| 2006/0264965 A1 | 11/2006 | Shadduck et al. | |
| 2006/0293756 A1 | 12/2006 | Felt | |
| 2007/0027546 A1 | 2/2007 | Palm | |
| 2007/0032874 A1 | 2/2007 | Lee et al. | |
| 2007/0050036 A1 | 3/2007 | Felt | |
| 2007/0233255 A1 | 10/2007 | Song et al. | |
| 2007/0244485 A1 | 10/2007 | Greenhalgh et al. | |
| 2008/0039942 A1 | 2/2008 | Bergeron | |
| 2008/0065220 A1 | 3/2008 | Alleyne et al. | |

(56) References Cited

U.S. PATENT DOCUMENTS

| | | | |
|---|---|---|---|
| 2008/0119853 A1 | 5/2008 | Felt et al. | |
| 2008/0125865 A1 | 5/2008 | Abdelgany | |
| 2008/0133017 A1 | 6/2008 | Beyer et al. | |
| 2008/0140206 A1 | 6/2008 | Felt | |
| 2008/0208343 A1 | 8/2008 | Felt | |
| 2008/0234820 A1 | 9/2008 | Felt et al. | |
| 2008/0249622 A1 | 10/2008 | Gray | |
| 2008/0262622 A1 | 10/2008 | Butler | |
| 2009/0069895 A1 | 3/2009 | Gittings et al. | |
| 2009/0138086 A1 | 5/2009 | Dewey | |
| 2009/0157186 A1 | 6/2009 | Magerl | |
| 2009/0270986 A1* | 10/2009 | Christensen | A61F 2/4465 623/17.14 |
| 2009/0276047 A1 | 11/2009 | Felt et al. | |
| 2010/0030338 A1 | 2/2010 | Simon | |
| 2010/0057144 A1 | 3/2010 | Felt et al. | |
| 2010/0145457 A1 | 6/2010 | Felt et al. | |
| 2011/0270399 A1 | 11/2011 | Yurek et al. | |
| 2017/0181866 A1 | 6/2017 | Felt et al. | |

FOREIGN PATENT DOCUMENTS

| | | |
|---|---|---|
| EP | 0 378 002 | 7/1990 |
| EP | 0 505 634 | 9/1992 |
| EP | 0 521 573 | 1/1993 |
| FR | 2781998 | 2/2000 |
| WO | WO 93/11723 | 6/1993 |
| WO | WO 95/30388 | 11/1995 |
| WO | WO 95/31946 | 11/1995 |
| WO | WO 95/31948 | 11/1995 |
| WO | WO 97/26847 | 7/1997 |
| WO | WO 98/20939 | 5/1998 |
| WO | WO 99/44509 | 9/1999 |
| WO | WO 1999/056800 | 11/1999 |
| WO | WO 99/61084 | 12/1999 |
| WO | WO 00/13619 | 3/2000 |
| WO | WO 00/59411 | 10/2000 |
| WO | WO 01/66021 | 9/2001 |
| WO | WO 2002/017821 | 3/2002 |
| WO | WO 03/099171 | 12/2003 |
| WO | WO 2004/098466 | 11/2004 |
| WO | WO 2005051246 | 6/2005 |
| WO | WO 2006051547 | 5/2006 |
| WO | WO 2006/127848 A2 | 11/2006 |
| WO | WO 2006/127849 A2 | 11/2006 |

OTHER PUBLICATIONS

Application and File history for U.S. Appl. No. 13/833,998, filed May 15, 2013, inventors Felt et al.
Application and File History for U.S. Appl. No. 11/372,357, filed Mar. 9, 2006, inventor Felt.
Application and File History for U.S. Appl. No. 11/900,205, filed Sep. 10, 2007, inventor Felt.
Application and File History for U.S. Appl. No. 11/900,209, filed Sep. 9, 2007, inventor Felt.
Application and File History for U.S. Appl. No. 11/372,477, filed Mar. 9, 2006, inventor Felt.
Application and File History for U.S. Appl. No. 12/435,087, filed May 4, 2009, inventor Felt.
Application and File History for U.S. Appl. No. 11/974,185, filed Oct. 11, 2007, inventor Felt.
Application and File History for U.S. Appl. No. 10/098,601, filed Mar. 15, 2002, inventor Felt.
Transaction History for U.S. Appl. No. 10/121,455, filed Apr. 12, 2002, inventor Felt.
Application and File History for U.S. Appl. No. 10/167,963, filed Jun. 12, 2002, inventor Felt.
Application and File History for U.S. Appl. No. 10/722,019, filed Nov. 24, 2003, inventor Felt.
Application and File History for U.S. Appl. No. 11/953,203, filed Dec. 10, 2007, inventor Felt.
Application and File History for U.S. Appl. No. 11/489,264, filed Jul. 19, 2006, inventor Palm.
Application and File History for U.S. Appl. No. 12/479,402, filed Jun. 5, 2009, inventor Felt.
Application and File History for U.S. Appl. No. 11/328,498, filed Jan. 9, 2006, inventor Sweeney et al.
Application and File History for U.S. Appl. No. 12/548,225, filed Aug. 26, 2009, inventors Felt et al.
Details of Second Office Action dated Mar. 26, 2012 for Chinese Application No. 200680018453.0.
Office Action dated Apr. 27, 2012 for Chinese Application No. 200780050196.3 English Translation not available.
Office Action dated Jan. 14, 2013 for Chinese Application No. 200780050196.3. English Translation not available.
Office Action dated Jun. 4,2010for Chinese Application No. 200680034261.9.
Search Report dated Mar. 21, 2012 for European Application No. EP06771111.
Office Action dated Jul. 19, 2013 for European Application No. 06771111.9.
Search Report dated Mar. 23, 2012 for European Application No. EP07853144.
Office Action dated Jul. 30,2013for Japanese Application No. 2009-538404.
Notice of Reasons for Rejection dated Sep. 18, 2012 for Japanese Application No. 2009-538404.
Office Action dated Feb. 1, 2011 for Japanese Application No. 2008-513686.
Notification of International Preliminary Report on Patentability dated Jun. 29, 2012 for PCT Application No. PCT/US06/20152.
Search Report dated Jul. 18, 2006 for PCT Application No. PCT/US2006/000558.
Preliminary Report on Patentability dated Jun. 4, 2009 for PCT Application No. PCT/US2007/024262.
Search Report dated Sep. 12, 2008 for PCT Application No. PCT/US06/20152.
IPRP and Written Opinion dated Sep. 25, 2014 for PCT Application No. PCT/US2013/032786.
Search Report and Written Opinion dated Aug. 19, 2013 for PCT Application No. PCT/US2013/032786.
An et al., "The Future of Spinal Fuzion. Txt." ORTHO SuperSite, Aug. 2006 pp. 1-3.
Andersson et al., "Macintosh Arthroplasty in Rheumatoid Arthritis," Department of Orthopaedic Surgery and Department of Rheumatology, The London Hospital, London, England, 1974, pp. 245-259.
Cameron et al., "Review of a Failed Knee Replacement and Some Observations on the Design of a Knee Resurfacing Prosthesis," Archives of Orthopaedic and Traumatic Surgery, vol. 97, No. 1, 1980, pp. 87-89.
Clary et al., "Experience with the MacIntosh Knee Prosthesis," Southern Medical Journal, Journal of the Southern Medical Association, Mar. 1972, vol. 65, No. 3, pp. 265-272.
Cluett, "Discetomy-Spinal Surgery to remove herniated disc", Nov. 29, 2005. 3 pages. http://orthopedica.about.com/cs/herniateddisk/a/repturedisk_3.htm.
Conaty, "Surgery of the Hip and Knee in Patients with Rheumatoid Arthritis," The Arthritis Servie (surgery) of Rancho, Los Amigos Hospital, Downey, Mar. 1973, vol. 55-A, No. 2, pp. 301-314.
Emerson et al., "The Use of the McKeever metallic Hemiarthroplasty for Unicompartmental Arthritis," The Journal of Bone and Joint Surgery, 1985, pp. 208-212.
Hackenberg et al., "Transforaminal lumbar interbody fusion: a safe technique with satisfactory three to five year results," Eur Spine J, 2005, pp. 551-558.
Hastings, "Double Hemiarthroplasty of the Knee in Rheumatoid Arthritis," The Journal of Bone and Joint Surgery, Feb. 1973, vol. 55 B, No. 1, pp. 112-118.
Jessop et al., "Follow-up of the Macintosh Arthroplasty of the Knee Joint," Rheum. Phys. Med., 1972, vol. XI, No. 5, pp. 224.
Kay et al., "The Macintosh Tibial Plateau Hemiprosthesis for the Rheumatoid Knee," The Journal of Bone and Joint Surgery, May 1972, vol. 54B, No. 2, pp. 256-262.

(56) References Cited

OTHER PUBLICATIONS

Kowalski et al., "Biomechanics of bone fusion," Neurosurg. Focus, Apr. 2001, vol. 10, pp. 1-7.
Kozinn et al., "Surgical Treatment of Unicompartmental Degenerative Arthritis of the Knee," Rheumatic Disease Clinics of North America, Dec. 1988, vol. 14, No. 3, pp. 545-564.
MacIntosh et al., "The Use of the Hemiarthroplasty Prosthesis for Advanced Osteoarthritis and Rheumatoid Arthritis of the Knee," The Journal of Bone and Joint Surgery, May 1972, vol. 54 B, No. 2, pp. 244-255.
McCallum et al., "Duplication of Medial Erosion in Unicompartmental Knee Arthroplasties," The Journal of Bone and Joint Surgery, 1995, pp. 726-728.
McCollum et al., "Tibial Plateau Prosthesis in Arthroplasty of the Knee," The Journal of Bone and Joint Surgery, Jun. 1970, vol. 52-A., No. 4, pp. 827-828.
McKeever, "Tibial Plateau Prosthesis," The Classic, pp. 3-12. Jan.-Feb. 1985.
Norton, "I:300 Interbody Fusion Device Technology Analysis," ABS Advanced Biosurfaces, Inc., Mar. 26, 2007, pp. 1-18.
Porter, "MacIntosh Athroplasty: a long-term review," J.R. Coll. Surg. Edinb., Aug. 1988, vol. 33, pp. 199-201.
Potter, "Arthroplasty of the Knee in Rheumatoid Arthritis and Osteoarthritis," The Journal of Bone and Joint Surgery, Jan. 1972, vol. 54-A, No. 1, pp. 1-24.
Potter, "Arthroplasty of the Knee with Tibial Metallic Implants of the McKeever and MacIntosh Design," Surgical Clinics of North America, Aug. 1969, vol. 49, No. 4, pp. 903-915.
Powers et al., "Minimally Invasive Fusion and Fixation Techniques," Neurosurg. Clin N Am, 2006, pp. 477-489.
RSB Spine, LLC, "510(k) Summary," Sep. 18, 2007, 4 pages, Cleveland, Ohio.
Ryortho, "Here comes ProDisc" Orthopedics This Week, vol. 2, Issue 3. (published prior to Jan. 19, 2006).
Sbarbaro, "Hemitibial plateau prosthesis ten years experience in 500 knee arthroplasties," Acta Orthopaedica Belgica, 1973, pp. 91-100.
Schorn et al., "MacIntosh Arthroplasty in Rheumatoid Arthritis," Rheumatology and Rehabilitation, vol. XVII, No. 3, pp. 155-163. 1978.
Scott et al., "McKeever Metallic Hemiarthroplasty of the Knee in Unicompartmental Degenerative Arthritis," The Journal of Bone and Joint Surgery, Feb. 1985, vol. 67-A, No. 2, pp. 203-207.
Spine-Tech, Inc., "Summary of Safety and Effectiveness," May 23, 2996, 100 pages, Minneapolis, Minnesota.
Wayne, "Use of the McIntosh Prosthesis in Surgical Reconstruction of the Knee," Abstracts of the 1971 Proceedings, Jun. 1972, No. 85, pp. 292-293.
Shin et al., "Posterior Lumbar Interbody Fusion via a Unilateral Approach," Yonsei Medical Journal, 2006, vol. 47, pp. 319-325.
Stauffer et al., "The MacIntosh Prosthesis, Prospective Clinical and Gait Evaluation," Arch Surg, Jun. 1975, vol. 110, pp. 717-720.
Steffen et al., "Effect of Implant Design and Endplate Preparation on the Compressive Strength of Interbody Fusion Constructs," SPINE, 2000, vol. 25, No. 9, pp. 1077-1084.
Swanson et al., "Unicompartmental and Bicompartmental Arthroplasty of the Knee with a Finned Metal Tibial-Plateau Implant," The Journal of Bone and Joint Surgery, Oct. 1985, vol. 67-A, No. 8, pp. 1175-1182.
Synthes Spine, "510 (k) Summary—Revised Sep. 2007" 5 pages, Sep. 14, 2007West Chester, Pennsylvania.
Tan et al., Interbody Device Shape and Size are Important to Strengthen the Vertebra—Implant Interface, SPINE 2005. vol. 30, No. 6, pp. 638-644.
Taylor et al., "MacIntosh arthroplasty in rheumatoid arthritis," Proceedings and Reports of Universities, Colleges, Councils and Associations, pp. 119-120.
Toth et al., "Polyehteretherketone as a biomaterial for spinal applications," Biomaterials, 2006, pp. 324-334.
Vadapalli et al., "Biomechanical Rationale for Using Polyetheretherketone (PEEK) Spacers for Lumbar Interbody Fusion—A Finite Element Study," SPINE, 2006, vol. 31, No. 26, pp. E992-E998.
Vertebral Technologies, "InterFuse® Interbody Fusion System," 2009, pamphlet.
Wordsworth et al., "MacIntosh Arthroplasty for the rheumatoid knee: a 10-year follow up," Annals of the Rheumatic Diseases, 1985, pp. 738-741.
Zwillich, Artificial Spinal Disc Nears Approval. WebMD Medical News. Nov. 29, 2005. 4 pages, http://www.webmd.com/content/article/88/9801.htm.
Get ADR.com Top Surgeons—Latest Orthopedic Options, Nov. 29, 2005, 2 pages, http://www.getadr.com/link.htm.
Get ADR.com Top Surgeons—Latest Orthopedic Options, Nov. 29, 2005, 2 pages, http://www.getadr.com/maverick.htm.
Application and File History for U.S. Appl. No. 15/363,295, filed Nov. 29, 2016, inventors Felt et al.

* cited by examiner

METHODS AND APPARATUS FOR MINIMALLY INVASIVE MODULAR INTERBODY FUSION DEVICES

RELATED APPLICATIONS

The present application is a continuation of U.S. application Ser. No. 15/682,033, filed Aug. 21, 2017, now U.S. Pat. No. 10,195,048, issued Feb. 5, 2019, which in turn is a continuation of U.S. application Ser. No. 11/974,185, filed Oct. 11, 2007, now U.S. Pat. No. 9,737,414, issued Aug. 22, 2017; which claims the benefit of U.S. Provisional Application No. 60/860,329 filed Nov. 21, 2006, each if which is incorporated herein in its entirety by reference.

FIELD OF THE INVENTION

The present invention relates generally to an implantable orthopedic fusion device for fusing joints in a patient such as a vertebral interbody fusion device. More particularly, the present invention relates to a rail-based modular interbody fusion device of predetermined size and shape.

BACKGROUND OF THE INVENTION

Joint fusion or arthrodesis is a common approach to alleviate the pain due to deteriorated and/or arthritic joints. Joint fusion involves inducing bone growth between two otherwise mobile bones in a joint, which alleviates pain by immobilizing and stabilizing the joint. The joint is generally fused in its most functional position. The ankle, wrist, finger, toe, knee and vertebral joints are all examples of joints that may be fused to alleviate pain associated with unstable, deteriorated joints.

The spinal motion segment consists of two adjacent vertebral bodies, the interposed intervertebral disc, as well as the attached ligaments, muscles, bony processes and the facet joints. The disc consists of the end plates at the surfaces of the vertebral bones, the soft inner core, called the nucleus pulposus and the annulus fibrosus ligament that circumferentially surrounds the nucleus and connects the vertebrae together. In normal discs, the nucleus cushions applied loads, thus protecting the other elements of the spinal motion segment. The nucleus in a normal disc responds to compression forces by bulging outward against the vertebral end plates and the annulus fibrosus. The annulus consists of collagen fibers and a smaller amount of elastic fibers, both of which are effective in resisting tension forces. However, the annulus on its own is not very effective in withstanding compression and shear forces.

As people age the intervertebral discs often degenerate naturally. Degeneration of the intervertebral discs may also occur in people as a result of degenerative disc disease. Degenerative disc disease of the spine is one of the most common conditions causing back pain and disability in our population. When a disc degenerates, the nucleus dehydrates. When a nucleus dehydrates, its ability to act as a cushion is reduced. Because the dehydrated nucleus is no longer able to bear loads, the loads are transferred to the annulus and to the facet joints. The annulus and facet joints are not capable of withstanding their increased share of the applied compression and torsional loads, and as such, they gradually deteriorate. As the annulus and facet joints deteriorate, many other effects ensue, including the narrowing of the interspace, bony spur formation, fragmentation of the annulus, fracture and deterioration of the cartilaginous end plates, and deterioration of the cartilage of the facet joints. The annulus and facet joints lose their structural stability and subtle but pathologic motions occur between the spinal bones. As the annulus loses stability it tends to bulge outward and may develop a tear allowing nucleus material to extrude. Breakdown products of the disc, including macroscopic debris, microscopic particles, and noxious biochemical substances build up. The particles and debris may produce sciatica and the noxious biochemical substances can irritate sensitive nerve endings in and around the disc and produce low back pain. Affected individuals experience muscle spasms, reduced flexibility of the low back, and pain when ordinary movements of the trunk are attempted.

Degeneration of a disc is irreversible. In some cases, the body will eventually stiffen the joints of the motion segment, effectively re-stabilizing the discs. Even in the cases where re-stabilization occurs, the process can take many years and patients often continue to experience disabling pain. Extended painful episodes of longer than three months often leads patients to seek a surgical solution for their pain.

Several methods have been devised to attempt to stabilize the spinal motion segment. Some of these methods include: applying rigid or semi-rigid support members on the sides of the motion segment; removing and replacing the entire disc with an articulating artificial device; removing and replacing the nucleus; and spinal fusion involving permanently fusing the vertebrae adjacent the affected disc.

Spinal fusion is generally regarded as an effective surgical treatment to alleviate back pain due to degeneration of a disc. The fusion process requires that the vertebral endplates be prepared by scraping the surface of the existing vertebral bone to promote bleeding and release of bone growth factors, and placing additional bone or suitable bone substitute onto the prepared surface. Devices of an appropriate size made from rigid materials such as metals (including titanium and tantalum), some plastics (including polyetheretherketone (PEEK), or carbon fiber-filled PEEK), and allograft bone (primarily from donor femurs) are commonly inserted into the prepared disc cavity as part of the interbody fusion procedure to help distract and stabilize the disc space and put the vertebra into proper position while the bone growth process takes place.

The interbody fusion procedure may be accomplished from an anterior, transforaminal, or a posterior surgical approach.

Most devices used in interbody spinal fusion require a relatively large opening that is typically larger than the dimensions of the rigid and unitary fusion device or cage that is to be inserted, examples of such devices include, U.S. Pat. No. 5,026,373 to Ray et al., U.S. Pat. No. 5,458,638 to Kuslich et al., and the NOVEL™ PEEK Spacers from Alphatec. In fact, many methods of interbody fusion, for example the method and device described in U.S. Pat. No. 5,192,327 to Brantigan, require bilateral placement of unitary devices through fairly large surgical openings. As with any surgical procedure, the larger the surgical access required, the higher the risk of infection and trauma to the surrounding anatomy.

There exists minimally invasive spinal fusion devices such as is disclosed in U.S. Pat. No. 5,549,679 to Kuslich and U.S. Pat. No. 6,997,929 to Manzi et al. The device disclosed in the U.S. Pat. No. 5,549,679 is a porous mesh bag that is filled in situ. The U.S. Pat. No. 6,997,929 is directed to a series of wafers that are vertically stacked to distract and support the vertebral endplates. U.S. Pat. No. 5,702,454 to Baumgartner discloses plastic beads which may be inserted one at a time into an intervertebral space on a flexible string. Further, U.S. Pat. No. 5,192,326 to Bao discloses hydrogel beads encased in a semi-permeable membrane.

While such minimally invasive technologies permit smaller access incision through the annulus (i.e. an annulotomy) to be used in a fusion procedure, the resulting fusion devices do not have the mechanical and dimensional features of the more rigid unitary fusion devices used in traditional surgical approaches and are less able to distract and stabilize the disc space. Thus, there is a need for a minimally invasive spinal fusion implant that could better emulate the mechanical and structural characteristics of a rigid unitary fusion device.

SUMMARY OF THE INVENTION

The present invention provides a method and apparatus for a rail-based modular interbody fusion device having a predetermined size and shape when assembled in situ. In one embodiment, the modular interbody fusion device comprises generally solid modular segments with rails that operably connect adjacent modular segments. This configuration allows the interbody spacer to be adapted for implantation via a small access incision or annulotomy.
through various surgical approaches, including a posterior or a lateral approach. In one embodiment, the rails operate with a sliding mechanism to connect and interlock adjacent modular segments. A stem portion of the rails that extends beyond the periphery of the body of the prosthesis is removable after implantation such that the modular segments combine to form a single device with a relatively smooth outer circumference when assembled in situ. The modular fusion device can be configured to provide full contact with and closely mimic the geometry of the surfaces of the joint being fused so as to more closely mimic the functionality of the largest existing rigid and unitary fusion devices.

In one embodiment, an interbody modular fusion device is adapted to be implanted in a prepared intervertebral space and includes at least three modular segments each having a width. The first modular segment has a first rail extending at least partially along one side of the width and beyond a periphery of the first modular segment. The second modular segment is slidably connected to the first rail on one side of the width and has a second rail extending at least partially along another side of the width and beyond a periphery of the second modular segment. The third modular segment is slidably connected to the second rail on one side of the width. The interbody fusion device has an expanded position in which the modular segments are extended along the first and second rails and positioned in a generally end to end configuration spaced apart by the rails prior to implantation. The interbody fusion device also has an implanted position in which the modular segments are positioned in a generally side by side configuration that defines a single assembled body having a generally continuous periphery that generally corresponds to the inner boundary of the annulus.

In one embodiment, each modular segment has a compressive modulus in the superior to inferior direction from about 0.5-15 GPa, such that the compressive modulus of the interbody fusion device generally corresponds to the compressive modulus of the surrounding cortical bone.

In one embodiment, locking features are provided to ensure that the modular interbody spacer is a unitary device both before and after insertion. To prevent the device from being separated prior to insertion, locking features may be provided on the rigid rails to prevent modular segments from being slid back off of the rails. This ensures that each modular segment is connected in its proper position and in the proper order. In addition, locking features may be provided on the modular segments to lock them together upon insertion. This prevents individual segments from dislocating from the assembled prosthesis and migrating outside of the annulus. Further, the interbody fusion device may include grooves, ridges, or other structures on its outer surface to contact surrounding bone and prevent the device from migrating out beyond the anterior limit of the intervertebral space.

Another aspect of the present invention comprises a method for implanting an interbody spacer. Because the modular interbody spacer may be implanted one segment at a time, a hole made in the annulus for implantation of the prosthesis may be a fraction of the size of the device in its final assembled form. The first modular segment is inserted into the intervertebral space through the small hole in the annulus. The second modular segment is then slid up the first rigid rail and into the intervertebral space until the second modular segment interlocks with the first modular segment. The tail stem of the first rigid rail is then severed from the device. This severing may be accomplished by simply snapping the rail off the device. Alternatively, the tail stem may be attached to the device by a screw, a bayonet mechanism, a twist lock or the like. As such, the rails may be removed from the device by unscrewing, or releasing the bayonet, etc. Subsequent modular segments are slid up the adjoining rigid rail into the interbody space and then interlocked with the previously inserted modular segment in a similar manner. Once all of the modular segments have been inserted and all of the tail stems severed, the modular interbody spacer is fully inserted into the patient's interbody space.

Another aspect of the present invention provides an insertion tool that may be used to aid in the insertion, positioning, and rail removal of the modular interbody spacer. The proximal end of the tool has a handle with an enclosed ratchet or roller mechanism attached to and in line with the inner lumen of an elongated tube at the distal end of the tool through which a rail may be inserted. The elongated tube may have a slit or other openings along the length of the tube to aid in threading the rails into the tube. The insertion tool may be provided with a cutting mechanism for removing the rails from the modular segments once they are fully inserted.

BRIEF DESCRIPTION OF THE DRAWINGS

The invention may be more completely understood in consideration of the following detailed description of various embodiments of the invention in connection with the accompanying drawings, in which.

DETAILED DESCRIPTION OF THE DRAWINGS

Figure 1:
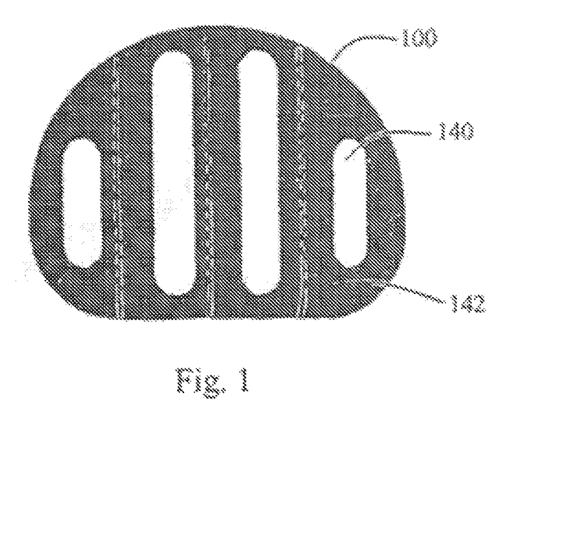
FIG. 1 is a top view of a modular interbody spacer according to an embodiment of the present invention in its inserted configuration.

Referring to FIG. 1, there can be seen a top view of a modular interbody spacer 100 according to an embodiment of the present invention as configured once inserted into the body. In this embodiment, modular disc prosthesis 100 comprises first 102, second 104, third 106, and fourth 108 modular segments. Interbody spacer 100 may be comprised of any suitable biomaterial, for example, a polymer, such as PEEK, a metal, such as titanium, trabecular metal, bone, or a resorbable material that may act as a scaffold for new bone growth and/or a carrier for stem cells.

Modular segments 102, 104, 106 and 108 may be inserted via a small annulotomy from a posterior or lateral approach. Interbody spacer 100 may then be constructed within the interbody space by first inserting modular segment 102 into the interbody space, then sliding modular segments 104, 106 and 108 along a series of rails wherein each segment locks with the previous segment to create an interbody spacer 100 having a final, assembled surface area that fully contacts and supports the vertebral end plates.

Interbody spacer 100 may include locking barbs that prevent individual units from backing out or extending beyond the anterior limit of the spacer. Spacer 100 may further include grooves, ridges 142 or other structures to engage the surrounding bone or otherwise prevent spacer 100 from backing out of the intervertebral space.

In a preferred embodiment, interbody spacer 100 may be made of PEEK having holes therethrough, allowing for tissue ingrowth thus promoting bony fusion. The holes 140 may be of varying size and shape. Holes 140 may be spaced apart on spacer 100 in any manner such that the compressive modulus of spacer 100 generally corresponds to the compressive modulus of the adjacent bone. Spacer 100 may also be of varying thicknesses to achieve the desired support and/or fusion of a particular intervertebral space, such as a lordotic configuration for L5-S1 fusion.

In an embodiment, prior to insertion, holes 140 of interbody spacer 100 may be packed or filled for example with, autologous bone graft, calcified or decalcified bone derivative, bone graft substitute, such as hydroxyapatite, agents to promote bone growth, such as bone morphogenetic protein, or osteogenic protein-1, antibiotics, anti-cancer agents, stem cells, biologically active cytokines, cytokine inhibitors, fibroblast growth factors, other osteoinductive and/or osteoconductive materials or any other material and combination thereof to promote fusion and/or stabilize the spinal motion segment.

In another embodiment, interbody spacer 100 may include surface modifications to provide for elution of medicants. Such medicants may include analgesics, antibiotics, anti-inflammatories, anticoagulants, antineoplastics or bioosteologics such as bone growth agents. In an alternative embodiment, spacer 100 may be comprised of a material, such as for example, porous PEEK, from which an imbibed medicant can elute. In yet another embodiment, an inner portion of the spacer 100 may be comprised of one material, while the outer portion is comprised of another material. For example, the inner portion may be comprised of a solid PEEK, while the outer portion is comprised of a porous PEEK. The surface of the porous PEEK may be coated with a bioactive agent or medicant. Spacer 100 may be imbedded with a radiopaque material, such as tantalum or titanium beads to allow for x-ray visualization of the implant.

In another embodiment, the rails may be used as fill tubes such that fill material may be injected or otherwise inserted into holes 140. Spacer 100 may also be manufactured to include channels or ducts 160 into which fill material may be inserted via the rails.

Figure 2:
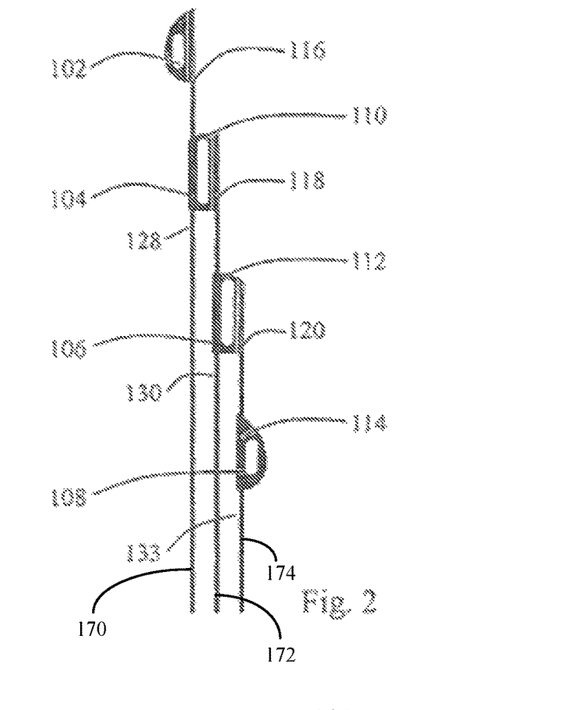
FIG. 2 is a perspective view of a modular interbody spacer according to an embodiment of the present invention at a first stage of insertion.

Referring to FIG. 2, there can be seen a portion of a modular interbody spacer 100 according to the preferred embodiment of the present invention prior to insertion into the intervertebral space. In alternate embodiments, the modular interbody spacer may comprise greater or fewer numbers of modular segments and rails.

Figure 3:
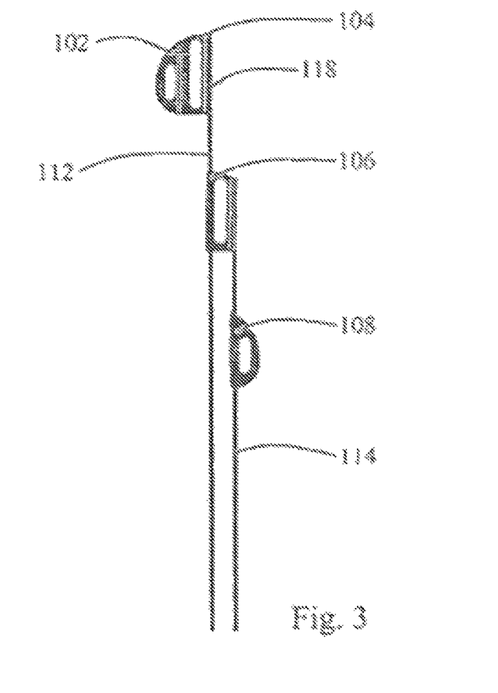
FIG. 3 is a perspective a view of a modular interbody spacer according to an embodiment of the present invention at a second stage of insertion.
Figure 4:
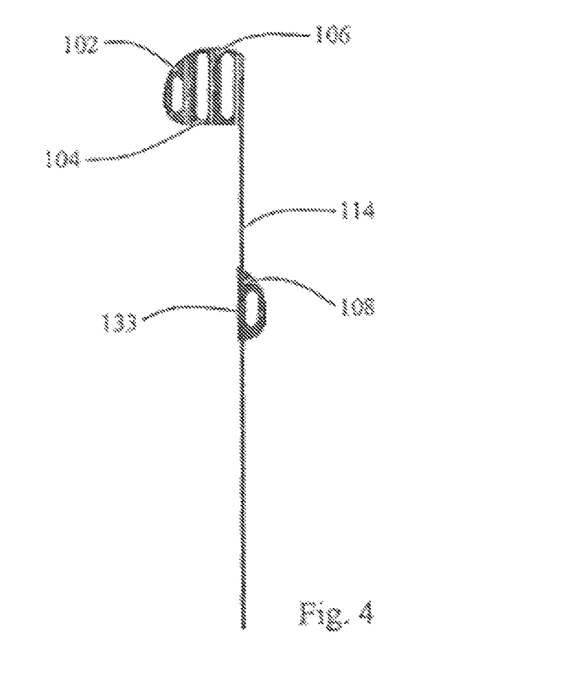
FIG. 4 is a perspective view of a modular interbody spacer according to an embodiment of the present invention at a final state of insertion.

Prior to insertion, modular interbody spacer 100 further includes first 110, second 112, and third 114 rails. First modular segment 102 is rigidly attached to first rail 110 at first segment interlocking portion 116. As shown in FIG. 3, second modular segment 104 is slidably attached to first segment interlocking portion 116 at first slot 128 and rigidly attached to second rail 112 at second segment interlocking portion 118. As shown in FIG. 4, third modular segment 106 is slidably attached to second interlocking portion 118 at second slot 130 and rigidly attached to third rail 114 at third segment interlocking portion 120. Fourth modular segment 108 is slidably attached to third rail 114 at fourth slot 133.

As shown in FIG. 2, each rail 110, 112 and 114 includes an elongated stem portion 170, 172, 174 that extends beyond a periphery of the body of the spacer 100, respectively. Preferably these stem portions 170, 172, 174 are long enough to permit access into the intervertebral space such that one modular segment can be positioned inside the intervertebral space while the next modular segment on the rail is still outside of the body. In an exemplary embodiment, the length of the stem portions 170, 172, 174 ranges between 6 cm-20 cm. Each rail 110, 112 and 114 may further include a retaining portion to keep the device from being separated prior to insertion. The retaining portions are configured to prevent the corresponding modular segments from sliding off the rails. The retaining portions may be molded into the rails or may be separate pieces or deformations of the rails added during the manufacture of the device. Rails 110, 112, 114 may be sequentially removed from the implant as modular segments 102, 104, 106, and 108 are connected within the intervertebral 5 space and moved laterally.

The preferred embodiment is an interbody spacer that is packaged, sterile, and ready for implantation at the surgical site. The package may include any number of modular segments. In a preferred embodiment, the package would include 5 individual modular segments. Single module packages may also be used so that the surgeon may use as many segments as desired. Since the device is fully preformed and delivered as a unitary implant, the device is under direct surgeon control until the interbody spacer is completely formed. This unitary design reduces the need for the surgeon to determine how to configure the spacer to allow for the most efficacious placement of the spacer in the intervertebral space and assures that the components' order of insertion and connection are properly achieved. The size and shape of the modular interbody spacer provides a final, assembled surface area that fully contacts and supports the vertebral end plates, stabilizing the spinal unit. In this regard, it will be understood that the modular interbody spacer 100 of the present invention may be provided in a variety of different final assembled sizes to correspond to different sizes of different intervertebral spaces.

Figure 5:
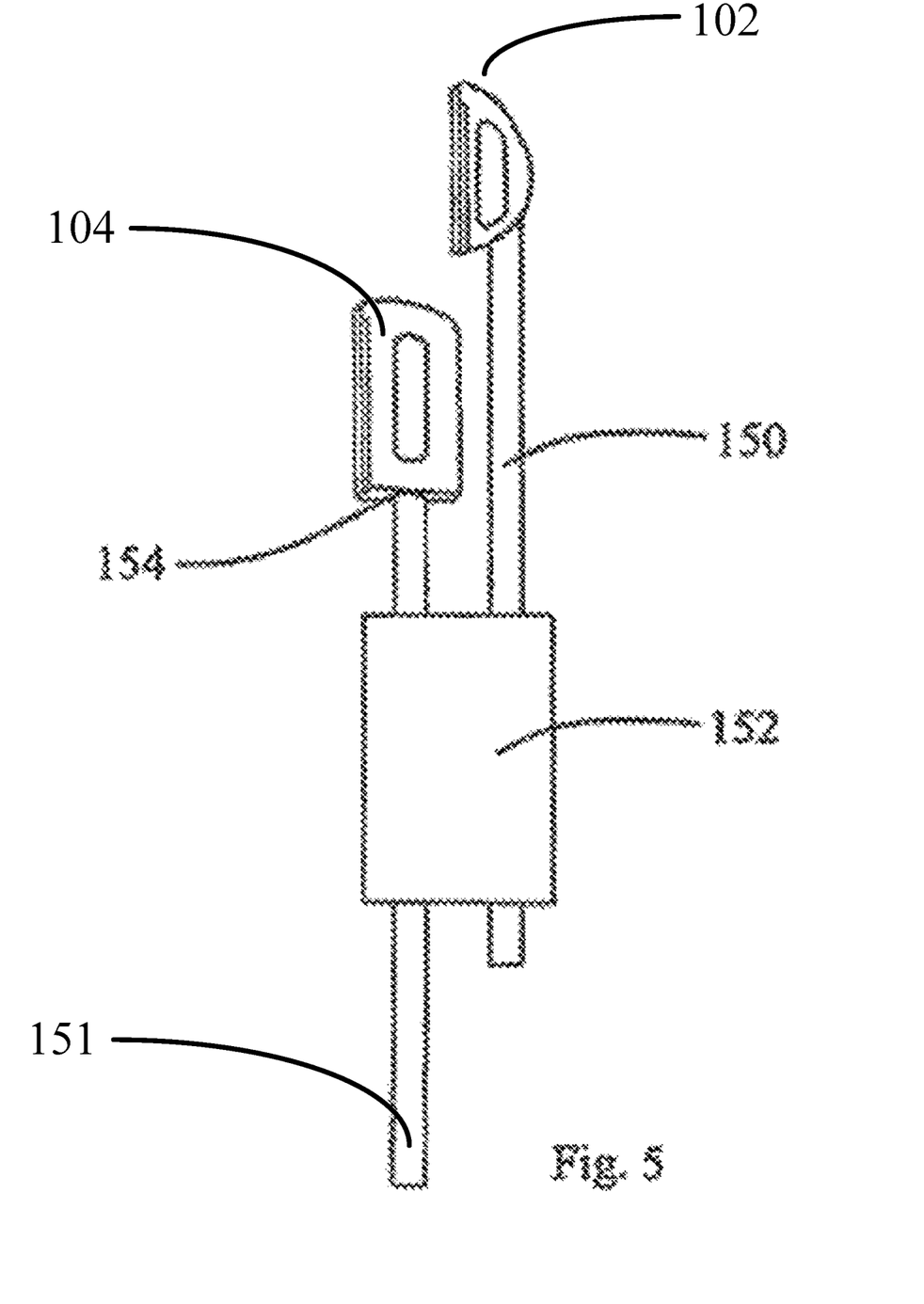
FIG. 5 is a perspective view of an alternate embodiment of the device.

In an alternative embodiment as shown in FIG. 5, separate guide rods 150, 151 and a guide mechanism 152 may be used to assist in inserting and aligning the modular segments. Rod 150, 151 may be attached to the proximal end of each modular segment. A first rod 150 may be used to insert a first modular segment 102 into position. A second guide rod 151 may be attached to a second modular segment 104 and used to place the second modular segment 104 in position to mate and interlock with the first modular segment 102. The first rod 150 could then be detached. Subsequent segments could be inserted by repeating the process.

In an embodiment, a modular segment may include a tapped hole 154 such that rod 150 may be screwed into hole 154. Rod 150 does not participate in the interlocking mechanism of modular segments. In an embodiment, rod 150 may either be made of the same material as the modular segments, or rod 150 may be comprised of a different material, including, but not limited to, plastics such as PEEK, or metals such as stainless steel or titanium. According to one aspect of the present invention, rod 150 may be integral to the modular segments. For example, rod 150 may be injection molded from a plastic or machined from a plastic or metal.

In another embodiment of the present invention, rod 150 may be formed separately from the modular segments and then joined to the modular segments via a mechanical method such as a mating thread, twist-lock, snap-lock or such, or by the use of adhesives or other material joining methods such as thermal and ultrasonic welding. One advantage to using a mechanical method of joining rod 150 to the modular segments is the potential to re-engage the modular segments for removal from the disc space, should the need arise. The removal sequence of rods 150 from the modular segments following implantation of the modular segments in the disc space is the same as for interlocking rails.

In an embodiment, modular interbody spacer 100 may be introduced through an access tube that is inserted partially into the intervertebral space. The access tube is at least 3 inches long and preferably about 6 inches long. It should be noted that although the insertion of modular intervertebral spacer 100 is described in relation to a four-segment embodiment, embodiments having any other number of segments would be inserted in a similar fashion.

During insertion, slots 128, 130, 133 slide along the stem portions 170, 172, 174 of rails 110, 112, 114 and onto segment interlocking portions 116, 118, 120. Slots 128, 130, 133 and segment interlocking portions 116, 118, 120 may be provided with locking features to prevent separation of modular segments 102, 104, 106 and 108. Locking features, such as a barb or stud or a series of barbs or studs, may be provided such that once a slot is slid onto a segment interlocking portion, it cannot be slid back off of it. A ratchet and pawl may also be used to lock modular segments together. A ratchet release tool may also be provided in case separation of modular 10 segments is desired once they are locked together.

Various modifications to the disclosed apparatuses and methods may be apparent to one of skill in the art upon reading this disclosure. The above is not contemplated to limit the scope of the present invention, which is limited only by the claims below.

The invention claimed is:

1. A modular interbody fusion device for fusing adjacent spinal vertebrae that is adapted to be implanted in a prepared interbody space, the device comprising:
   a first modular segment having a first width including a first rail, the first rail having an elongated stem portion and extending at least partially along one side of the first width of the first modular segment, the elongated stem portion having a length of 6 to 20 centimeters;
   a second modular segment having a second width and a body portion structure on one side of the second width slidably connectable to the stem portion of the first rail; and
   an insertion guide rod and guide mechanism for sliding the second modular segment along the stem portion of the first rail to mate and interlock with the first modular segment wherein the device has an implanted position in which the modular segments are positioned in a generally side by side configuration that defines a unitary body including multiple holes therethrough adapted for tissue ingrowth and adapted to contact and support adjacent vertebra,
   wherein one or more insertion guide rods, including the insertion guide rod, may be mechanically attached to and detached from one or more modular segments thus allowing assembly of the fusion device through an access tube that is inserted partially into the intervertebral space;
   and wherein the modular interbody fusion device is a unitary implant such that the first modular segment, the second module segment, the insertion guide rod, and the guide mechanism, are pre-assembled in an expanded position from which the second modular segment slides along the stem portion of the first rail to interlock with the first modular segment via the insertion guide rod and guide mechanism.

2. The modular fusion device of claim 1 wherein each of the multiple holes couples to a channel in the unitary body to enable a fill material to be injected through each channel and into each one of the multiple holes.

3. The modular fusion device of claim 2 wherein the fill material is selected from the group consisting of: bone graft, bone graft substitute, agents to promote bone growth, antibiotics, anti-cancer agents, stem cells, fibroblast growth factors, bone derivative, biologically active cytokines, cytokine inhibitors, osteoconductive material, osteoinductive material and any combination thereof.

4. The modular fusion device of claim 1 wherein the one or more additional modular segments can be slidably connected sequentially to a previous modular segment wherein the device has an implanted position in which the first modular segment, the second modular segment and the one or more modular segments are positioned in a generally side by side configuration that defines a unitary body.

5. The modular fusion device of claim 1, wherein the second modular segment includes a second rail extending at least partially along another side of the second width of the second modular segment.

6. The modular fusion device of claim 1, wherein the multiple holes vary in size and shape.

7. The modular fusion device of claim 1, wherein each of the multiple holes is elongated.

8. The modular fusion device of claim 1, wherein each of the modular segments is manufactured from a material selected from the group consisting of titanium, trabecular metal, polyetheretherketone (PEEK), carbon-filled PEEK, or mixtures thereof.

9. The modular fusion device of claim 1, wherein the multiple holes are spaced in a manner such that a compressive modulus of the unitary body corresponds to a compressive modulus of the adjacent spinal vertebrae.

* * * * *